United States Patent [19]

Barnett et al.

[11] Patent Number: 5,612,482
[45] Date of Patent: Mar. 18, 1997

[54] PROCESS FOR PREPARING 5-SUBSTITUTED PYRROLO-[2,3-D]PYRIMIDINES

[75] Inventors: Charles J. Barnett, Indianapolis; Thomas M. Wilson, Speedway, both of Ind.

[73] Assignee: Eli Lilly and Company, Indianapolis, Ind.

[21] Appl. No.: 594,971

[22] Filed: Jan. 31, 1996

Related U.S. Application Data

[62] Division of Ser. No. 362,392, Dec. 22, 1994, which is a division of Ser. No. 66,831, May 24, 1993, Pat. No. 5,416,211, which is a continuation-in-part of Ser. No. 951,515, Sep. 25, 1992, abandoned.

[51] Int. Cl.⁶ .................................................. C07D 487/02
[52] U.S. Cl. .................................................. 544/280
[58] Field of Search .................................................. 544/280

[56] References Cited

U.S. PATENT DOCUMENTS

| | | | |
|---|---|---|---|
| 4,997,838 | 3/1991 | Akimoto et al. | 214/258 |
| 5,235,053 | 8/1993 | Barnett et al. | 544/280 |
| 5,278,307 | 1/1994 | Barnett et al. | 544/280 |
| 5,403,843 | 4/1995 | Akimoto et al. | 514/258 |
| 5,426,187 | 6/1995 | Barnett et al. | 544/280 |

FOREIGN PATENT DOCUMENTS 402903  12/1990  European Pat. Off. .

OTHER PUBLICATIONS

Miwa, et al., *J. Med. Chem.*, 34, 555–560 (1991).
Noell, C.W., et al., *J. Heterocyclic Chem.*, 1, 34–41 (1964).
Kandasamy Ramasamy, et al., *J. Chem. Soc. Chem. Commun.* 560–562 (1989).
Secrist, J.A., et al., *J. Org. Chem.*, 43, 3937–3941 (1978).
DeGraw, J. I., et al., *J. Med. Chem.*, 25, 1227–1230 (1982).
Taylor, C. E., et al., *J. Org. Chem.*, 55, 3222–3227 (1990).

*Primary Examiner*—Matthew V. Grumbling
*Attorney, Agent, or Firm*—Margaret M. Brumm; David E. Boone

[57] ABSTRACT

Processes for preparing 5-substituted pyrrolo[2,3-d]pyrimidines which are useful as intermediates for the preparation of pyrrolo[2,3-d]pyrimidine antineoplastic agents or as antineoplastic agents themselves are provided.

16 Claims, No Drawings

PROCESS FOR PREPARING 5-SUBSTITUTED PYRROLO-[2,3-D]PYRIMIDINES

CROSS REFERENCE

This application is a division of application Ser. No. 08/362,392, filed on Dec. 22, 1994, which is a division of application Ser. No. 08/066,831, filed on May 24, 1993, now U.S. Pat. No. 5,416,216, which is a continuation-in-part of application Ser. No. 07/951,515, filed on Sep. 25, 1992, now abandoned.

FIELD OF THE INVENTION

The invention relates to the field of pharmaceutical and organic chemistry and provides a process for preparing 5-substituted pyrrolo[2,3-d]pyrimidine derivatives useful as intermediates in the preparation of therapeutically active pyrrolo[2,3-d]pyrimidine-based antifolates.

BACKGROUND OF THE INVENTION

Compounds known to have antifolate activity are well recognized as chemotherapeutic agents for the treatment of cancer. One such agent, methotrexate, is now one of the most widely used anticancer drugs; and many other compounds in the folic acid family have been synthesized, tested and discussed in the chemical and medical literature. The compounds have various activities at the enzymatic level. In particular, they inhibit such enzymes as dihydrofolate reductase, folate polyglutamate synthetase, glycinamide ribonucleotide formyltransferase and thymidylate synthase.

More recently, a series of 4-hydroxypyrrolo[2,3-d]pyrimidine-L-glutamic acid derivatives have been disclosed and shown to be particularly useful antifolate drugs. See, e.g., Akimoto, et al., European Patent Publication 0 434 426.

5-Substituted pyrrolo[2,3-d]pyrimidine compounds of the formula I

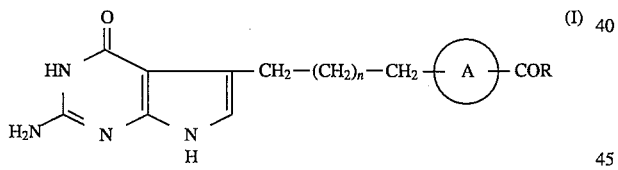

wherein

R is $NHC^*H(COOR^1)CH_2CH_2COOR^1$ or $OR^1$;

each $R^1$ is H or the same or different carboxy protecting group;

the configuration about the carbon atom designated * is L;

n is 0 or 1; and

Ⓐ is an aryl group which may be substituted, are useful in preparing various 5-substituted pyrrolo[2,3d]pyrimidine-based therapeutic agents or, when R is $NHC^*H(COOR^1)CH_2CH_2COOR^1$ and each $R^1$ is H, or a salt thereof, are useful as therapeutic agents.

The art recognizes multiple methods for the preparation of pyrrolopyrimidine derivatives. See, e.g., U.S. Pat. No. 4,997,838; Miwa, et al., *J. Med. Chem.*, 34:555–560 (1991); C. W. Noell, et al., *J. Heterocyclic Chem.*, 1:34–41 (1964); Kandasamy Ramasamy, et al., *J. Chem. Soc., Chem. Commun.*, 560–562 (1989); and John A. Secrist, et al., *J. Org. Chem.*, 43: 3937–3941 (1978).

The present invention provides regiospecific processes for preparing 5-substituted pyrrolo[2,3-d]primidines which are useful as intermediates for the preparation of, inter alia, pharmaceutically active pyrrolo[2,3-d]pyrimidine compounds, or as pharmaceutically active compounds.

The present invention further provides a regiospecific process for preparing 5-substituted pyrrolo[2,3-d]pyrimidine compounds, wherein said process is carried out in the same vessel.

SUMMARY OF THE INVENTION

This invention provides a process for preparing 5-substituted pyrrolo[2,3-d]pyrimidines of formula I

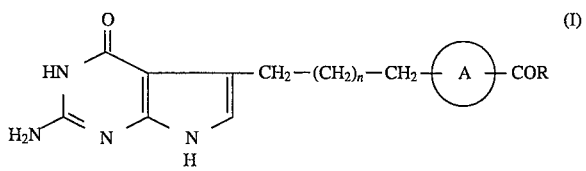

wherein

R is $NHC^*H(COOR^1)CH_2CH_2COOR^1$ or $OR^1$;

each $R^1$ is H or the same or different carboxy protecting group;

the configuration about the carbon atom designated * is L;

n is 0 or 1; and

Ⓐ is an aryl group which may be substituted;

or a salt thereof, which comprises a) reacting 2,4-diamino-6-hydroxypyrimidine with a haloaldehyde of formula II

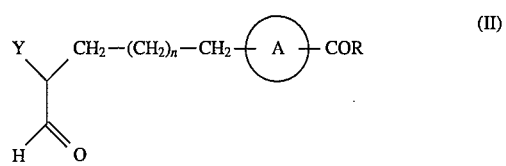

wherein

Y is bromo, chloro or iodo; and

Ⓐ, R, $R^1$, A and * are as defined above; and b) optionally salifying the reaction product from step a).

The present invention also provides a process for preparing 5-substituted pyrrolo[2,3-d]pyrimidines of formula I

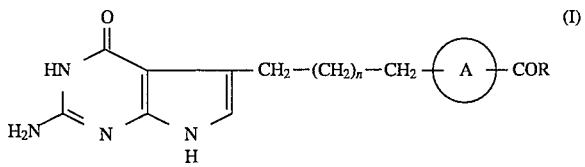

wherein R, $R^1$, Ⓐ, n and * are as defined above, or a salt thereof, which comprises a) reacting a halogenating agent with a compound of formula III

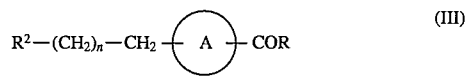

wherein

R, $R^1$, Ⓐ, n and * are as defined above; and $R^2$ is a substituent of formula IV, V, or VI

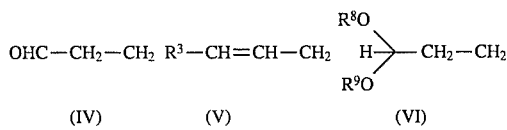

(IV)     (V)     (VI)

wherein $R^3$ is $OR^4$, wherein $R^4$ is a hydroxy protecting group;

$OCOR^5$, wherein $R^5$ is $C_1-C_6$ alkyl, phenyl, benzyl or $C_3-C_6$ cycloalkyl;

$NR^6R^7$, wherein $R^6$ and $R^7$ are independently $C_1-C_6$ alkyl, $C_3-C_6$ cycloalkyl, or are taken together with the nitrogen atom and, optionally, an oxygen atom, to form a 5- to 6-membered saturated monocyclic group which optionally may be substituted with one or two substituents selected from the group consisting of $C_1-C_4$ alkyl and $C_1-C_4$ alkoxy; or $R^8$ and $R^9$ each are $C_1-C_4$ alkyl or are taken together with the oxygen atoms to form a 5- to 6-membered saturated monocyclic group which optionally may be substituted with one or two substituents selected from the group consisting of hydroxy, $C_1-C_4$ alkyl, and $C_1-C_4$ alkoxy;

b) reacting the reaction product from step a) with 2,4-diamino-6-hydroxypyrimidine; and c) optionally salifying the reaction product from step b).

DETAILED DESCRIPTION OF THE INVENTION

Throughout this document, all temperatures are in degrees Celsius and all expressions of proportion, percentage, and the like, are in weight units, except for solvents or mixtures thereof which are in volume units.

The term "$C_1-C_4$ alkyl" refers to straight or branched aliphatic chains of 1–4 carbon atoms such as, for example, methyl, ethyl, propyl, isopropyl, n-butyl, isobutyl, sec-butyl and tert-butyl.

The term "$C_1-C_6$ alkyl" refers to $C_1-C_4$ alkyl plus the straight and branched aliphatic chains of 5–6 carbon atoms including, for example, n-pentyl, isopentyl, neopentyl, n-hexyl, isohexyl, 3-methylpentyl, 2,3-dimethylbutyl, and the like.

The term "aryl", as used in describing the ring structure identified as (A) in formulae I, II, III, and VII refers to 5- to 6-membered aromatic residues, including heterocyclic groups containing up to three heteroatoms (e.g., N, O and S) contained therein, such as, for example, phenyl, especially 1,4-phenylene, thienyl, pyridyl, furyl, and the like. Such aryl groups optionally may be substituted, in addition to the COR group, with one or two substituent groups selected from halo, hydroxy, $C_1-C_4$ alkyl, and $C_1-C_4$ alkoxy. Other than unsubstituted 1,4-phenylene, a single additional substitution of (A) at the 2-position relative to the 1-position COR functionality is preferred.

The term "$C_1-C_4$ alkoxy" refers to an alkyl group of 1 to 4 carbon atoms attached through an oxygen bridge such as for example, methoxy, ethoxy, n-propoxy, isopropoxy, and the like.

The term "halo" refers to bromo, chloro, fluoro and iodo.

The term "$C_3-C_6$ cycloalkyl" refers to a saturated hydrocarbon ring group having from 3 to 6 carbon atoms including, for example, cyclopentyl and cyclohexyl.

As used herein, the carboxy protecting group of $R^1$, where $R^1$ is other than H, and the hydroxy protecting group of $R^4$ denote groups which generally are not found in the final therapeutic compounds but are intentionally introduced during a portion of the synthetic process to protect a group which otherwise might react in the course of chemical manipulations, and is later removed. Since compounds bearing one or more protecting groups are of importance primarily as chemical intermediates (although some protected derivatives also exhibit biological activity), their precise structure is not critical. Numerous reactions for the formation and removal of such protecting groups are described in a number of standard works including, for example, *Protective Groups in Organic Chemistry*, Chapter 3 (McOmie Ed., Plenum Press, 1973); Green, *Protective Groups in Organic Synthesis*, Chapter 2 (John Wiley, 1981); and Schroder and Lubke, *The Peptides*, Vol. I (Academic Press, 1965).

Carboxy groups can be protected as an ester group which is selectively removable under sufficiently mild conditions so as not to disrupt the desired structure of the molecule. Esters suitable for use in protecting the carboxy group include branched $C_1-C_6$ alkyl esters such as t-butyl, and esters substituted with (i) $C_1-C_4$ alkoxy such as methoxymethyl, 1-methoxyethyl, ethoxyethyl, and the like; (ii) $C_1-C_6$ alkylthio such as methylthiomethyl, 1-ethylthioethyl and the like; (iii) halo such as 2,2,2-trichloroethyl, 2-bromoethyl, 2-iodoethoxycarbonyl, and the like; (iv) 1 to 3 phenyl groups each of which may be unsubstituted or mono-, di-, or tri-substituted with $C_1-C_6$ alkyl, $C_1-C_4$ alkoxy, hydroxy, halo and nitro such as 4-nitrobenzyl; or (v) aroyl such as phenacyl. When more than one carboxy group is present, each carboxy protecting group may be the same or may be different. It is preferred that each is the same group. Preferred protecting groups are $C_1-C_6$ alkyl esters such as methyl ester or ethyl ester.

Preferred hydroxy protecting groups include ether groups such as $C_1-C_4$ alkyl ether, phenyl ether, and silyl ether. Particularly useful silyl ether groups include, for example, tri-isopropylsilyl ether, trimethylsilyl ether, triethylsilyl ether, and t-butyldimethylsilyl ether (see, e.g., Colvin, E. W., *Silicon Reagents in Organic Synthesis*, (Academic Press, 1988).

The compounds of formula I exist in tautomeric equilibrium with the corresponding 4(3H)-oxo compounds. For illustrative purposes, the equilibrium for the pyrrolopyrimidine ring system, and the numbering thereof, are shown below:

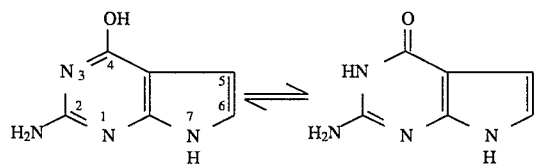

For convenience, the 4(3H)-oxo form is depicted in formula I, and the corresponding nomenclature is used throughout this specification. However, it is understood that such depictions include the corresponding tautomeric 4-hydroxy form.

The present process requires reacting 2,4-diamino-6-hydroxypyrimidine with a haloaldehyde of formula II in a solvent, under conditions which favor cyclization.

The 2,4-diamino-6-hydroxypyrimidine starting material employed in the present process is commercially available, whereas preparation of the haloaldehydes of formula II, when R is $OR^1$ and $R^1$ is H or a carboxy protecting group, is known in the art (see, e.g., DeGraw, et al., *J. Med. Chem.*, 25:1227–1230 (1982).

DeGraw teaches the preparation of a formula II compound where (A) is 1,4-phenylene, n is 0, R is $OR^1$, and $R^1$ is H. Methods for protection of the carboxylic acid group and preparation of a formula II compound where n is 1 are well known.

An alternative starting material for formula II is prepared by condensing an enol ether of formula VII

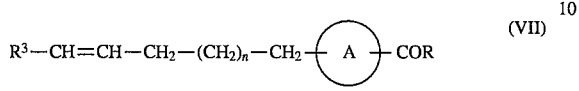

wherein (A) is an aryl group which may be substituted;

R is $OR^1$;

$R^1$ is H or a carboxy protecting group;

n is 0 or 1;

$R^3$ is $OR^4$; and $R^4$ is a hydroxy protecting group, as generally described by DeGraw, supra, with a compound of formula VIII

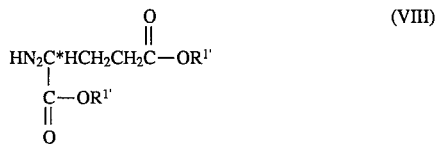

wherein each $R^{1'}$ is the same or different carboxy protecting group and the configuration about the carbon atom designated * is L, using conventional condensation techniques. One preferred condensation method, when R of a formula II compound is H, is taught by Taylor, et al., in U.S. Pat. No. 4,684,653. Otherwise, a formula II compound should first be deprotected prior to condensation.

Upon completion of condensation, the reaction product is halogenated via known procedures (see, e.g. DeKimpe, supra) using an appropriate halogenating agent, to give a formula II starting material where R is $NHC^*H(COOR^1)CH_2CH_2COOR^1$, Y is bromo, chloro or iodo, and $R^1$, n and * are as defined above.

Particularly appropriate halogenating agents include, for example, elemental bromine, chlorine, and iodine, N-bromo-, N-chloro-, and N-iodosuccinimide, N-bromo-, N-chloro-, and N-iodophthalimide, and the like.

Thus, this first aspect of the present invention provides a process for preparing 5-substituted pyrrolo[2,3-d]pyrimidines of formula I

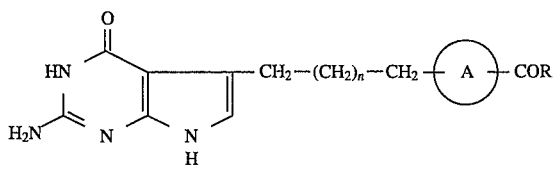

wherein

R is $NHC^*H(COOR^1)CH_2CH_2COOR^1$ or $OR^1$;

each $R^1$ is H or the same or different carboxy protecting group;

the configuration about the carbon atom designated * is L;

n is 0 or 1; and (A) is an aryl group which may be substituted;

or a salt thereof, which comprises a) reacting 2,4-diamino-6-hydroxypyrimidine with a haloaldehyde of formula II

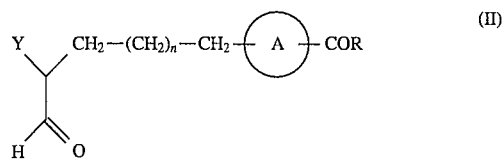

wherein

Y is bromo, chloro or iodo; and (A), R, $R^1$, n and * are as defined above; and b) optionally salifying the reaction product from step a).

The above-described reaction is run in the presence of an appropriate solvent which includes, for example, $C_1$–$C_4$ alcohol, acetonitrile, dimethylformamide (DMF), dimethylsulfoxide (DMSO), dimethylacetamide, N-methylpyrrolidinone, water, and mixtures thereof. Preferred is a mixture of solvents which includes ethanol and water, or acetonitrile and water.

The amount of time needed for this reaction to run to completion will be recognized by one of ordinary skill in the art. Chromatographic techniques such as TLC and HPLC will assist in determining the completion of this reaction.

The temperature employed in this step should be sufficient to effect completion of this reaction. Typically, temperature ranges from about 25° C. to about 100° C. are preferred, while a range from about 70° C. to about 90° C. is especially preferred.

Otherwise, formula I compounds prepared by this process are readily isolated by ordinary procedures and require no further purification for use as intermediates.

Another aspect of the present invention is a process for preparing 5-substituted pyrrolo[2,3-d]pyrimidines of formula I which comprises a) reacting a halogenating agent with a compound of formula III

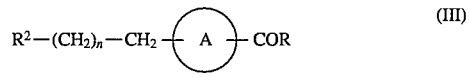

wherein

R, $R^1$, (A), n and * are as defined above; and $R^2$ is a substituent of formula IV, V, or VI

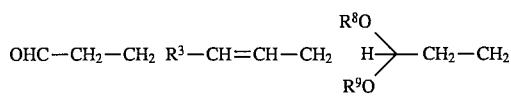

wherein $R^3$ is $OR^4$, wherein $R^4$ is a hydroxy protecting group;

$OCOR^5$, wherein $R^5$ is $C_1$–$C_6$ alkyl, phenyl, benzyl or $C_3$–$C_6$ cycloalkyl;

$NR^6R^7$, wherein $R^6$ and $R^7$ are independently $C_1$–$C_6$ alkyl, $C_3$–$C_6$ cycloalkyl, or are taken together with the nitrogen atom and, optionally, an oxygen atom, to form a 5- to 6-membered saturated monocyclic group which optionally may be substituted with one or two substituents selected from the group consisting of $C_1$–$C_4$ alkyl and $C_1$–$C_4$ alkoxy; or $R^8$ and $R^9$ each are $C_1$–$C_4$ alkyl or are taken together with the oxygen atoms to form a 5- to 6-membered saturated monocyclic group which optionally may be substituted with one or two substituents selected from the group consisting of hydroxy, $C_1$–$C_4$ alkyl, and $C_1$–$C_4$ alkoxy;

b) reacting the reaction product from step a) with 2,4-diamino-6-hydroxypyrimidine; and c) optionally salifying the reaction product from step b).

The preparation of an aldehyde of formula III (where $R^2$ is a substituent of formula IV) is known in the art (see, e.g. Taylor, et al., *J. Med. Chem.*, 55:3222–3227 (1990).

Taylor teaches the preparation of a formula III compound where R is $OR^1$, $R^1$ is methyl, n is 0 or 1, and $R^2$ is a substituent of formula IV. The aldehyde of formula III may further be modified to form enamines, enol esters, enol ethers, (where $R^2$ is a substituent of formula V), and acetals (where $R^2$ is a substituent of formula VI), by processes known in the organic chemical art. Thus, the starting material of this aspect of the present invention includes the aldehyde, enol ether, enol ester, enamine and acetal forms of formula III compounds.

An enol ether of formula III where R is $OR^1$, $R^1$ is a carboxy protecting group, $R^2$ is a substituent of formula V, $R^3$ is $OR^4$, and $R^4$ is a hydromy protecting group (especially methyl) is the preferred formula III starting material.

Alternatively, an enol ether starting material of formula III may be prepared by condensing the above-described, preferred enol ether of formula III with a compound of formula VIII as described above. Formula III compounds, where R is $OR^1$ and $R^1$ is a carboxy protecting group preferably are deprotected prior to condensation. However, it is preferred to carry out this condensation following completion of the instant process.

Once a formula III starting material is selected and added to an appropriate solvent, it is first reacted with a halogenating agent, and the reaction product from the first step is reacted with 2,4-diamino-6-hydroxypyrimidine. The reaction product from this step optionally may be salified using conventional procedures.

Appropriate and preferred solvents, temperature, reaction time and isolation procedures for this process are as described above for the cyclization of compounds of formula II compounds to compounds of formula I.

In the preparation of formula I compounds using the present process, each step may be carried out independently wherein the reaction product from each step is isolated and purified or, preferably, carried out in situ as a process wherein each step of the process is sequentially carried out in the same vessel.

Formula I compounds, when R is $OR^1$, and $R^1$ is H or a carboxy protecting group, or when R is $NHC^*H(COOR^1)CH_2CH_2(COOR^1)$, and $R^1$ is the same or different carboxy protecting group, are intermediates useful for the preparation of, inter alia, therapeutically active pyrrolo[2,3-d]pyrimidine antifolate agents.

When R is $OR^1$ and $R^1$ is H, or, following the preferred deprotection step when $R^1$ is a carboxy protecting group, a formula I compound first must be condensed with a compound of formula VIII above. Following condensation, if $R^1$ is H, the product is in a final form which is ready for pharmaceutical use. If $R^1$ is a carboxy protecting group, such a protecting group may be removed and the resulting product is a therapeutically active antifolate.

Likewise, a formula I compound, when R is $NHC^*H(COOR^1)CH_2CH_2(COOR^1)$ and $R^1$ is H, is therapeutically active as a reaction product of the processes of the present invention. Otherwise, when $R^1$ is a carboxy protecting group, it, too, must be removed by standard methods to provide a therapeutically active agent.

Once therapeutically active pyrrolo[2,3-d]pyrimidine antifolates are prepared, conversion to a salt form will provide more pharmaceutically-acceptable compounds.

The following examples illustrate specific aspects of the present invention and are not intended to limit the scope thereof in any respect and should not be so construed.

PREPARATION 1

Methyl 4-(4-trimethylsilyloxy-3-butenyl)benzoate

To 3.65 g (17.7 mmol) of 4-(4-carbomethoxyphenyl)butanal and 3.43 g (21.2 mmol) of 1,1,1,3,3,3-hexamethyldisilazane in 177 ml of methylene chloride in a nitrogen atmosphere was added 3.89 g (19.5 mmol) trimethylsilyl iodide at −15° C. over 2 minutes. The mixture was stirred for 10 minutes then allowed to come to room temperature. After 2 hours, the excess reagent was quenched by addition of 100 ml water. The layers were separated and the organic phase dried over sodium sulfate. The solvent was removed by vacuum concentration to give 5.0 g of methyl 4-(4-trimethylsilyloxy-3-butenyl)benzoate in a yield of 100 percent. Thin Layer Chromatography (TLC) analysis (silica; hexane - ethyl acetate 3:2) indicated that the above product was substantially pure, b.p. 170° C. @0.12 torr. $^1$H NMR ($CDCl_3$)δ0.15 (s, 9H), 2.41 (q, J=7.2 Hz, 2H), 2.69 (m, 2H), 3.89 (s, 3H), 4.47 (q, J=7.2 Hz, 1H), 6.15 (m, 1H), 7.25 (d, J=8.2 Hz, 2H), 7.93 (d, J =8.2 Hz, 2H); $^{13}$C NMR ($CDCl_3$) δ−0.60, 25.0, 35.9, 51.8, 109.8, 128.4, 128.5, 129.6, 138.6, 148.0, 167.1; FDMS 279 (90), 278 ($M^+$, 100%) 280, 251, 226; An analytical sample was obtained by flash chromatography (silica; hexane - ethyl acetate 3:2). Anal. for $C_{15}H_{22}O_3Si$, Calcd: C, 64.71; H, 7.96; Found: C, 64.90; H, 8.05.

PREPARATION 2

2-Bromo-4-(4-carbomethoxyphenyl)butanal

To 4.46 g (16 mmol) of methyl 4-(4-trimethylsilyloxy-3-butenyl) benzoate, prepared in Preparation 1, in 16 ml carbon tetrachloride at −20° C. was slowly added 2.56 g (16 mmol) of bromine in 16 ml carbon tetrachloride over 4 hours. The mixture was allowed to come to room temperature then decanted from a small amount of insoluble material. The solvent was removed by vacuum rotary evaporation to give 4.60 g of 2-bromo-4-(4-carbomethoxyphenyl)butanal. Chromatography purification (silica; hexane - ethyl acetate 7:3) of the above product gave 4.0 g in a yield of 87.8 percent. $^1$H NMR ($CDCl_3$) δ2.24 (m, 1H), 2.36 (m, 1H), 2.81 (m, 1H), 2.90 (m, 1H), 3.90 (s, 3H), 4.16 (m, 1H), 7.27 (d, J=8.2 Hz, 2H), 7.97 (d, J=8.2 Hz, 2H), 9.46 (d, J=2.1 Hz, 1H); $^{13}$C NMR ($CDCl_3$) δ32.5, 32.7, 51.7, 54.3, 128.3, 128.4, 129.8, 145.0, 166.6, 192.0.

EXAMPLE 3

4-(2-[2-Amino-4-oxo-3,7-dihydropyrrolo[2,3-d]pyrimidin-5-yl]ethyl)benzoic acid methyl ester To 1.69 g (13.4 mmol) of 2,4-diamino-6-hydroxypyrimidine, 2.20 g (26.8 mmol) of sodium acetate and 20 ml of water at 80° C. were added 3.82 g (13.4 mmol) of 2-bromo-4-(4-carbomethoxyphenyl)butanal, prepared in Preparation 2, in 7 ml of methanol over 5 minutes. The mixture was maintained at 80° C. for 5 minutes, cooled to room temperature and stirred for 30 minutes. The mixture was filtered, washed with water, and dried for 18 hours at 50° C. @10 torr to provide 3.32 g of 4-(2-[2-amino-4-oxo-3,7-dihydropyrrolo[2,3 -d]pyrimidin-5-yl]ethyl)benzoic acid methyl ester (m.p. >220° C.) in a yield of 79.4 percent. The remaining filtrate was cooled to 5° C. and filtered to provide an additional 0.069 g of the above product, for a combined yield of 81 percent. $^1$H NMR (DMSO-$d_6$)δ2.80 (m, 2H), 2.93 (m, 2H), 3.78 (s, 3H), 5.97 (s, 2H), 6.26 (d, J =2.0 Hz, 1H), 7.28 (d, J=8.2 Hz, 2H), 7.80 (d, J=8.2 Hz, 2H), 10.12 (s, 1H), 10.58 (s, 1H); FDMS 312 (M$^+$), Anal. for $C_{16}H_{16}N_4O_3$, Calcd: C, 61.53; H, 5.16; N, 17.94; Found: C, 61.79; H, 5.33; N, 17.66.

PREPARATION 4

4-[2-(2-Amino-4,7-dihydro-4-oxo-3H-pyrrolo[2,3-d]pyrimidin-5-yl)ethyl]benzoic acid A mixture of 3.17 g (10.15 mmol) of 4-[2-(2-amino-4,7-dihydro-4-oxo-3H-pyrrolo[2,3-d]pyrimidin-5yl)ethyl]benzoic acid methyl ester, prepared in Example 3, in 30 ml of 1N aqueous sodium hydroxide and 5 ml methanol was stirred for 20 hours at room temperature. Tetrahydrofuran (5 ml) was added and the mixture was stirred for 4 hours then neutralized with 30 ml of 1N aqueous hydrochloric acid. The resulting precipitate was separated by filtration, washed with water (20 ml) and dried in a vacuum oven at 50° C. to obtain 2.65 g of the above product in a yield of 87 percent. $^1$H NMR (DMSO-$d_6$) δ2.45 (m, 2H), 2.91 (m, 2H), 5.99 (s, 2H), 6.27 (d, J=2.0 Hz, 1H), 7.27 (d, J=8.2 Hz, 2H), 7.79 (d, J=8.2 Hz, 2H), 10.14 (s, 1H), 10.59 (d, J=2.0 Hz, 1H), 13.2 (bs, 1H).

PREPARATION 5

N-[4-[2-[2-Amino-4,7-dihydro-4-oxo-3H-pyrrolo[2,3-d]pyrimidin-5-yl]ethyl]benzoyl]glutamic acid dimethyl ester To 2.00 g (6.74 mmol) of 4-[2-(2-amino-4,7-dihydro-4-oxo-3H-pyrrolo[2,3-d]pyrimidin-5-yl)ethyl]benzoic acid, prepared in Preparation 4, in 23 ml dimethylformamide under nitrogen was added 1.40 g (13.8 mmol) of N-methylmorpholine and 1.17 g (6.70 mmol) of 4-chloro-2,6-dimethoxytriazine. The formation of the active ester was monitored by the HPLC analysis of aliquots. After 40 minutes at room temperature 0.70 g (6.9 mmol) of N-methylmorpholine was added followed by 1.56 g (7.37 mmol) L- glutamic acid dimethyl ester hydrochloride. After 30 minutes HPLC analysis indicated substantially complete consumption of the active ester and formation of N-[4-[2-[2-Amino-4,7-dihydro-4-oxo-3H-pyrrolo[2,3-d]pyrimidin-5-yl]ethyl]benzoyl]glutamic acid dimethyl ester. The reaction mixture was filtered and the above product concentrated and purified by silica gel chromatography (elution 1:4 methanol:methylene chloride). The pure fractions were pooled and provided 1.30 g of the above product in a yield of 43 percent. $^1$H NMR (DMSO-$d_6$) δ2.01 (m, 2H), 2.40 (t, J =7.4 Hz, 2H), 2.80 (m, 2H), 2.92 (m, 2H), 3.53 (s, 3H), 3.59 (s, 3H), 4.40 (m, 1H), 5.99 (s, 2H),6.26 (d, J=1.9 Hz, 1H), 7.23 (d, J=8.2 Hz, 2H), 7.73 (d, J=8.2 Hz, 2H), 8.62 (d, J=7.5 Hz, 1H), 10.15 (s, 1H), 10.57 (d, J =1.9 Hz, 1H ).

PREPARATION 6

N-[4-[2-[2-Amino-4,7-dihydro-4-oxo-3H-pyrrolo[2,3-d]pyrimidin-5-yl]ethyl]benzoyl]glutamic acid A mixture of 0.50 g (1.1 mmol) of N-[4-[2-[2-amino-4,7-dihydro-4-oxo-3H-pyrrolo[2,3-d]pyrimidin-5-yl]ethyl]benzoyl]glutamic acid dimethyl ester, prepared in Preparation 5, and 3.3 ml of 2N aqueous sodium hydroxide was stirred at room temperature for 48 hours and neutralized to a pH of 5 with 6M aqueous hydrochloric acid. The precipitate was filtered, washed with water and dried, to give 0.277 g of the above product in a yield of 59 percent.

PREPARATION 7

1-Methoxy-4-(4-carboxymethylphenyl)-1-butene

To 3.77 g (11 mmol) of methoxymethyltriphenyl phosphonium chloride in 10 ml of toluene at 0° C. under nitrogen was added 11 ml (11 mmol) of 1M potassium t-butoxide in tetrahydrofuran over 20 minutes. The resulting solution was stirred for 10 minutes, then 1.92 g (10 mmol) of 3-(4-carboxymethylphenyl)-propanal in 10 ml of toluene was added over 15 minutes. After stirring the mixture for 20 minutes 40 ml of ethyl ether were added. The resulting precipitate was filtered with diatomaceous earth, collected, washed with 20 ml of water, 20 ml of saturated sodium chloride and dried with a 9:1 sodium sulfate: saturated sodium chloride mixture. Vacuum concentration of the filtered solution and trituration of the residue with hexane gave 1.72 g of 1-methoxy-4-(4-carboxymethyl phenyl)-1-butene. Chromatography of the above product (silica gel, 8:2 hexane: ethyl acetate) gave 1.0 g of a mixture of geometric isomers (Z/E - 6:4) of the above product in a combined yield of 45 percent. b.p. 140° C. @0.07 torr. $^1$H NMR (CDCl$_3$) δ2.23 (dq, J=1.0, 8.1 Hz), 2.40 (dq, J =1.3, 8.0 Hz) total 2H, 2.70 (t, J=8.1 Hz), 2.71 (t, J =8.0 Hz), total 2H, 3.48 (s), 3.55 (s), total 3H, 3.89 (s), 3.90 (s), total 3H, 4.32 (q, J=6.2 Hz), 4.71 (dt, J =7.3, 12.6 Hz), total 1H, 5.87 (dt, J=1.3, 6.2 Hz), 6.28 (dt, J=1.0, 12.6 Hz ), total 1H, 7.23 (d, J=8.2 Hz ), 7.27 (d, J=8.2 Hz), total 1H, 7.94 (d, J=8.2 Hz), 7.95 (d, J=8.2 Hz), total 2H; $^{13}$C NMR (CDCl$_3$) δ25.2, 29.3, 36.0, 37.4, 51.9, 56.0, 59.5, 101.8, 101.9, 105.5, 127.9, 128.0, 128.5, 128.6, 129.6, 129.7, 146.9, 147.5, 147.9, 148.0, 167.1, 167.2; IR (CHCl$_3$) 3025, 2954, 1716, 1656, 1610, 1437, 1284, 1112 cm$^{-1}$; MS(FD) m/z 220 (M$^+$).

EXAMPLE 8

4-(2-[2-amino-4(1H)-oxo-4,7-dihydropyrrolo[2,3-d]pyrimidin-5-yl]ethyl)benzoic acid methyl ester To 1.10 g ( 5.0 mmol) of the 1-methoxy-4-(4-carboxymethylphenyl)-1-butene, prepared in Preparation 7, in 10 ml of acetonitrile was added 10 ml of water. The resulting mixture was cooled to 5° C. and 0.80 g (1.0 equiv) of bromine were added. A 0.63 g (5.0 mmol) of 2,4-diamino-6-hydroxypyrimidine was added and the mixture was stirred and warmed to 80° C. After 40 minutes the mixture was cooled to room temperature and 20 ml of water were added. The pH of the resulting slurry was adjusted to 6 with 5N sodium hydroxide. The precipitate was collected by filtration, washed with water, and dried at 50° C. @10 torr to obtain 1.44 g of the above product in a yield of 92 percent.

EXAMPLE 9

4-(2-[2-amino-4(1H)-oxo-4,7-dihydropyrrolo[2,3-d]pyrimidin-5-yl]ethyl)benzoyl-L-glutamic acid diethyl ester To 300 mg (0.766 mmol) of N-4-(1-methoxy-1-buten-4-yl)benzoyl-L-glutamic acid diethyl ester, 3.0 ml of acetonitrile, and 3.0 ml of water, stirred at room temperature, are added 122 mg (0.766 mmol) of bromine in 1 ml of acetonitrile. To this solution is added 188 mg (2.3 mmol) of sodium acetate and 0.97 mg (0.77 mmol) of 2,4-diamino-6-hydroxypyrimidine and the resulting mixture is heated to 60° C. for 18 hours, cooled, then concentrated under vacuum. The resulting residue is triturated (2×5 ml of water) and decanted. Ethanol (5 ml) and 440 mg (2.3 mmol) of p-toluenesulfonic acid monohydrate are added. After heating under reflux for 20 minutes the mixture is cooled to room temperature and filtered. The precipitate is washed with ethanol (2×5ml) and dried to obtain a p-toluenesulfonate salt of the title compound.

The present invention has been described in detail, including the preferred embodiments thereof. However, it will be appreciated that those skilled in the art, upon consideration of the present disclosure, may make modifications and/or improvements that fall within the scope and spirit of the invention as set forth in the following claims.

What is claimed is:

1. A process for preparing 5-substituted pyrrolo[2,3-d] pyrimidines of formula I

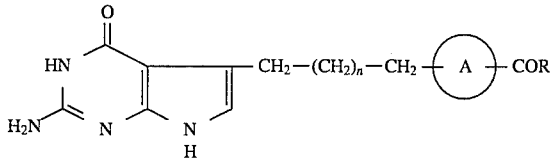

wherein

R is NHC*H(COOR$^1$)CH$_2$CH$_2$COOR$^1$ or OR$^1$;

each R$^1$ is H or the same or different carboxy protecting group;

the configuration about the carbon atom designated * is L;

n is 0 or 1;

Ⓐ is an aryl group which may be substituted; or a salt thereof, which comprises a) reacting a halogenating agent with a compound of formula III

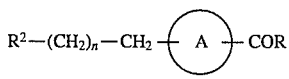

wherein

R, R$^1$, Ⓐ, n and * are as defined above; and

R$^2$ is a substituent of formula V,

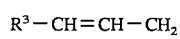

wherein R$^3$ is

OR$^4$, wherein R$^4$ is a hydroxy protecting group;

OCOR$^5$, wherein R$^5$ is C$_1$–C$_6$ alkyl, phenyl, benzyl or C$_3$–C$_6$ cycloalkyl; or NR$^6$R$^7$, wherein R$^6$ and R$^7$ are independently C$_1$–C$_6$ alkyl, C$_3$–C$_6$ cycloalkyl, or are taken together with the nitrogen atom and, optionally, an oxygen atom, to form a 5- to 6- membered saturated monocyclic group which optionally may be substituted with one or two substituents selected from the group consisting of C$_1$–C$_4$ alkyl, and C$_1$–C$_4$ alkoxy;

b) reacting the reaction product from step a) with 2,4-diamino-6-hydroxypyrimidine; and c) optionally salifying the reaction product from step b).

2. The process of claim 1 wherein the halogenating agent is elemental bromine or chlorine.

3. The process of claim 1 wherein R is OR$^1$; R$^1$ is H or a carboxy protecting group; R$^3$ is OR$^4$; R4 is a hydroxy protecting group; and Ⓐ is 1,4-phenylene.

4. The process of claim 3 wherein R$^1$ is a carboxy protecting group.

5. The process of claim 4 wherein R$^1$ group is methyl.

6. The process of claim 5 wherein n is 0.

7. The process of claim 6 wherein R$^4$ is methyl.

8. The process of claim 7 wherein the halogenating agent is elemental bromine or chlorine.

9. The process of claim 1 wherein R is NHC*H(COOR$^1$)CH$_2$CH$_2$COOR$^1$; R$^1$ is H or the same or different carboxy protecting group; R$^3$ is OR$^4$; R$^4$ is a hydroxy protecting group; and Ⓐ is 1,4-phenylene.

10. The process of claim 9 wherein each R$^1$ is a carboxy protecting group.

11. The process of claim 10 wherein each R$^1$ group is ethyl.

12. The process of claim 11 wherein n is 0.

13. The process of claim 12 wherein R$^4$ is methyl.

14. The process of claim 13 wherein the halogenating agent is elemental bromine or chlorine.

15. The process of claim 1 wherein steps a) and b) are carried out in the same vessel.

16. The process of claim 1 wherein steps a), b), and c) are carried out in the same vessel.

* * * * *